United States Patent [19]
Rottem

[11] Patent Number: 6,032,678
[45] Date of Patent: Mar. 7, 2000

[54] ADJUNCT TO DIAGNOSTIC IMAGING SYSTEMS FOR ANALYSIS OF IMAGES OF AN OBJECT OR A BODY PART OR ORGAN

[75] Inventor: Shraga Rottem, 69-40 Fleet St., Forest Hills, N.Y. 11375

[73] Assignee: Shraga Rottem, Forest Hills, N.Y.

[21] Appl. No.: 09/042,269

[22] Filed: Mar. 13, 1998

Related U.S. Application Data

[60] Provisional application No. 60/039,073, Mar. 14, 1997.

[51] Int. Cl.$^7$ ...................................................... A61B 10/00
[52] U.S. Cl. ........................ 128/920; 600/425; 600/437; 128/922
[58] Field of Search ..................................... 600/547, 595, 600/437, 407, 425; 128/920, 921, 922, 923, 924; 382/132, 276; 364/419.08

[56] References Cited

U.S. PATENT DOCUMENTS

| | | |
|---|---|---|
| 5,235,510 | 8/1993 | Yamada et al. ........................ 128/922 |
| 5,251,131 | 10/1993 | Masand et al. ..................... 364/419.08 |
| 5,799,100 | 8/1998 | Clarke et al. ............................ 382/132 |
| 5,850,465 | 12/1998 | Shimura et al. ........................ 128/920 |

*Primary Examiner*—William E. Kamm
*Assistant Examiner*—Ali M. Imam
*Attorney, Agent, or Firm*—Graham & James LLP

[57] ABSTRACT

An adjunct device and system which works in tandem with existing diagnostic imaging tools such as for medical diagnosis to enhance reliability of diagnosis with guidance for appropriate treatment or imaging devices for machinery (or other objects) and guidance for repair. The adjunct device initially analyzes an input image and either automatically or semi-automatically (with input from a grid of organ and anomalies) provides matching images for adjacent viewing and comparison. Where relevant, the device provides weighted possible diagnoses with advisory pathways for treatment or additional testing. The device and system include computer elements with stored medical data appropriate to the diagnostic tool being used and the body part(s) or objects, being diagnosed to provide the appropriate comparative image.

4 Claims, 16 Drawing Sheets

Glossary - Alphabetical List

| A-B | Cerclage sutures | Cystadenoma, ov. | Chron's disease |
|-----|---|---|---|
| C-D | Cervical cancer | CystadenoCa., ov. | Cumulus oophorus |
| E-F | Cervix, congenital malf. | Colon cancer | Daughter cyst, ov. |
| G-H | Cervical fibroid | Contraction, uterine | D&C, false route |
| I-J | Cervical incl. cyst | Cornual pregn. | Decidual reaction |
| K-L | Cervical mucus | Cornual pregn., reduct. | Degenerat. intralig. fibr. |
| M-N | Cervical polyp | Corpus luteum cyst | Degenerat. intraut. fibr. |
| O-P | Cervical pregnancy | Corpus luteum, normal | Degenerat. pedunc. fibr. |
| Q-R | Cervical pregn., reduct. | Corpus luteum haemmor. | Dermoid cyst |
| S-T | Cervical stenosis, postmenop. | Corpus luteum, pregn. | Dysgerminoma |
| U-V | | | |
| W-X | | | |
| Y-Z | | | |

ADJUNCT TO DIAGNOSTIC IMAGING SYSTEMS FOR ANALYSIS OF IMAGES OF AN OBJECT OR A BODY PART OR ORGAN

This application claims priority from the filing date of the U.S. Provisional Application 60/039,073 filed on Mar. 14,1997.

FIELD OF THE INVENTION

This invention relates to devices used as adjuncts to diagnostic imaging systems and devices and particularly to such device adjuncts used for analysis of images of human body organs for the enhancement of correctness of diagnosis thereof by existing diagnostic devices.

BACKGROUND OF THE INVENTION

The need for conducting a scan such as for medical purposes or for generally determining a particular state of a person or object is triggered by one of three basic factors. In a first instance, the person complains of various symptoms (or an object is similar to other objects which have been exhibiting defects). Secondly the person or object is already being checked for some unrelated reason and an anomaly appears which requires further investigation, or thirdly there is simply an inquiry for the conducting of a screening test to determine (or to rule out) a specific or suspected state or condition (e.g., a prospective parent simply wishing to observe a sonogram of an unborn child).

The basic diagnostic methods of determining the health conditions of a patient, or whether there are anomalies in a patient's medical condition, are primarily:
 (a) direct interviews with the patient for the subjective determination of not overtly apparent symptoms (e.g., pain) and conditions, and
 (b) the imaging of affected areas of the patient's body for an objective determination (regardless of whether the patient is complaining of a symptom or something was found based on testing for an unrelated condition or state).

The type of imaging most properly utilized for an initial objective determination is usually dictated by the nature of the organ or part of the body exhibiting a specific condition (or which is being tested for determining if a condition exists), or the actual condition which is suspected.

Imaging devices (the term "imaging" used hereinafter includes optical, aural and any other sensory recordable state of an object or patient) primarily include those which permit visual inspection of a site or cavity directly or by use of a lens system for optical enhancement, and devices which permit visual inspection of a site through analog or digital displays or the analysis of images resulting from the use of ultrasound waves (sonograms), magnetic resonance (MRI), computerized tomography (CAT scans), nuclear medicine, x-rays or other imaging technology. Existing specific tools or devices used for imaging include laparoscopes, MRI and ultrasonogram devices, as well as hysteroscopes, arthroscopes, esophagoscopes, bronchoscopes, rectoscopes, laryngoscopes, otoscopes, ophthalmoscopes, colposcopes, microscopes, computed radiography, x-ray imaging, computed tomography, mammography, angiography, gamma camera and nuclear medicine instruments, boreoscopes (used for internal analysis of machinery) and the like, which are all well known diagnostic tools in the art.

Results from use of an imaging devices are usually directly visually (or less often, aurally) analyzed by skilled technicians (e.g., structural analysis of objects such as aircraft for metal fatigue or other possible defects) or medical personnel (i.e., diagnosticians) for determination of abnormalities or the lack thereof, in deciding on a probable basis for a condition or even for the determination that a condition does not exist. However, even with skilled analyzers, anomalies may be slight, obscured, or even not abnormal in the patient being tested since, while generally similar, body parts and organs are rarely sufficiently different in appearance between patients, whereby, unless specifically recognized, diagnostic results may be in error.

To assist in making a diagnosis from an image scanning, oftentime "landmarks" of an object or an organ are designated as being indicative of anomalies and the portion of the image related to the landmark is digitized and computer analyzed with a stored database. This comparison serves to determine whether the portion falls within accepted normal parameters or not, in providing an automatically generated diagnosis. Examples of such systems, with respect to medical diagnosis, are disclosed in U.S. Pat. Nos. 5,235,510 and 5,437,278.

Though the original image remains available for the diagnostician in such computer aided systems, there is little enhancement to the actual analysis by the diagnostician of the image itself except for some indication where and what to look for more closely, in determining the veracity of the digitized analysis. In addition, the results from the digitization are only as valid as the data originally input with acceptance of a diagnosis serving to take away decisional control from the diagnostician. Furthermore, the devices are entirely geared to simple diagnosis based on a comparison between digitized portions of an image and a stored data base. There is however no guidance with respect to appropriate additional tests, probability of correctness of diagnosis and probability of mistake of the diagnosis (with reasons or basis for the possible errors), follow ups, treatment and the like.

SUMMARY OF THE INVENTION

It is an object of the present invention to provide a multi-tier diagnostic and treatment, repair and monitoring or follow up advisory system wherein the diagnostician retains comparative control, with a direct comparison of library images (normal and abnormal images closely related to patient type) to the real time image of the patient's organ or body type (or object being imaged), regardless of imaging device utilized.

It is a further object of the present invention to provide the diagnostic and treatment advisory system whereby the system advises the diagnostician, in various stages, of the probability of likely conditions, errors which may result in incorrect diagnoses, the necessary steps or tests for refinement of the diagnoses, treatment relevant to the diagnoses and conditions for re-examination.

Generally the present invention comprises an adjunct for an existing diagnostic and treatment or diagnostic and repair system which is adapted for use by an operator with existing organ and body imaging devices or machinery diagnostic and repair systems and the like. The system comprises:
 a) means for providing comparative images for a diagnostician to directly compare on a single display, the image obtained from the patient (or object) and library stored images (from the same type of screening device), corresponding to probable conditions as determined either by the diagnostician or by computerized comparison to the library stored images falling within preset comparison parameters;

b) means for providing weighted probability for a particular diagnosis being relevant to the patient's (or object's) condition, based on library stored general parameters and optionally in further view of the patient's prior medical history (or repair or maintenance history);

c) means for providing weighted probability for a particular mistake being relevant to the patient's (or object's) condition and image based on library stored general parameters and optionally in further view of the patient's prior medical history (or object's prior history) and present image on the screen. (The means also provides a showing of probable errors with respect to a particular selected image).

d) means for providing to the diagnostician, if relevant, which additional test are required to increase the probability of relevance of a probable diagnosis;

e) means for providing to the diagnostician, information regarding treatment or repair protocols for a diagnosis with a probability above a pre-set probability level.

f) means for providing the user or diagnostician case and situation directions for monitoring and follow-up.

These and other objects, features and advantages of the present invention will become more evident from the following discussion and the drawings in which:

SHORT DESCRIPTION OF THE DRAWINGS

FIG. 12 is a view of a display showing access through a glossary of condition and organ information;

DETAILED DESCRIPTION OF THE INVENTION

Figure 1:
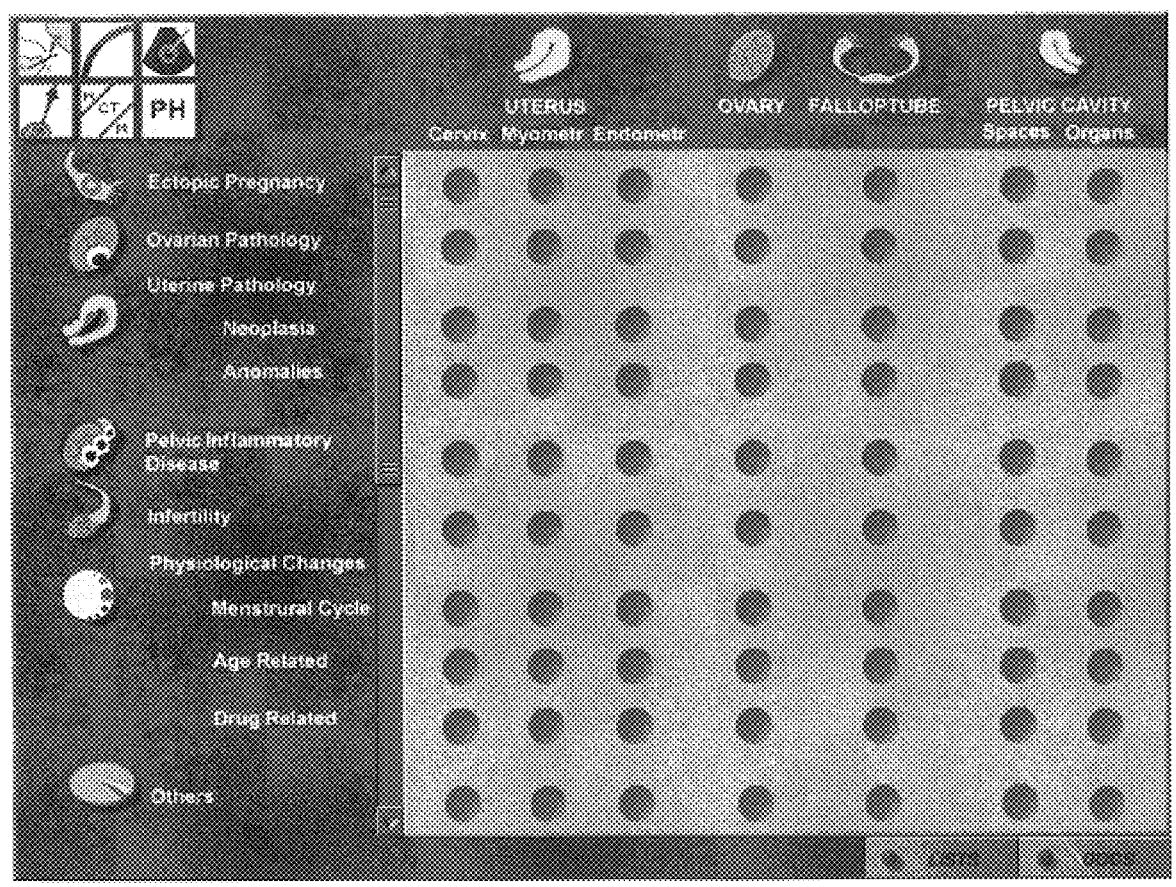
FIG. 1 is a view of a display showing a matrix of gynecological organs and conditions or complained of symptoms.

With the operation of the present invention, initial subjective and objective observations are utilized to determine the nature of an initial screening such as a pelvic examination for a gynecological problem (the problem having been suspected for reasons as outlined above). The various organs relevant to the condition are screened with an appropriate device such as with a laparoscope and the images obtained are stored and analyzed by a computer by sites of interest for possible conditions. The analysis is made, as in the prior art, from answers to a generated questionnaire regarding condition of various "landmarks" of the image (in sophisticated systems, the computer itself can scan and determine the answers with respect to the "landmarks"). A matrix of possible conditions relative to organs is generated. The operator or diagnostician then determines, with guidance, the most probable diagnoses and checks definitions of the various conditions which are available at hand with specifics regarding factors which are indicative of the condition. When a match is determined to have occurred between a basis for condition and the actual image obtained, with a probability above a threshold level, the operator activates the portion of the matrix of the intersection between organ and suspected condition. An example of an organ having the suspected condition is displayed for direct visual comparison with the stored image of the patient and a probability of correct diagnosis is assessed. With the selection of the condition and related image, the operator is also advised of conditions for error and the various possibilities which can lead to error. Selection of different condition and comparative image continues until the most likely conditions are obtained on a probability basis. The device of the present invention provides guidance, in the form of recommendations for the conducting of additional test regimens, e.g., x-rays, to further refine the selected diagnoses for a most likely diagnosis, with caveats with respect to other conditions if the diagnosis is in error. The diagnostician is also guided to explore conditions which may have resulted in a diagnoses but wherein additional conditions may be responsible for such diagnoses being in error.

When the most likely diagnosis has been arrived at with elimination of errors, the device provides guidance with respect to follow ups (e.g., return visits for additional testing, with conditions which change in a specific manner as indicative of the existence of a condition, within a non-health threatening time period) and a regimen of treatment.

After the procedure is completed, a report may be generated which includes the diagnosis, both the actual image and corresponding library matched image, and a listing of probable errors with matching error images (i.e. similar but probably erroneous for reasons listed).

DETAILED DESCRIPTION OF THE DRAWING AND THE PREFERRED EMBODIMENTS

Figure 5:
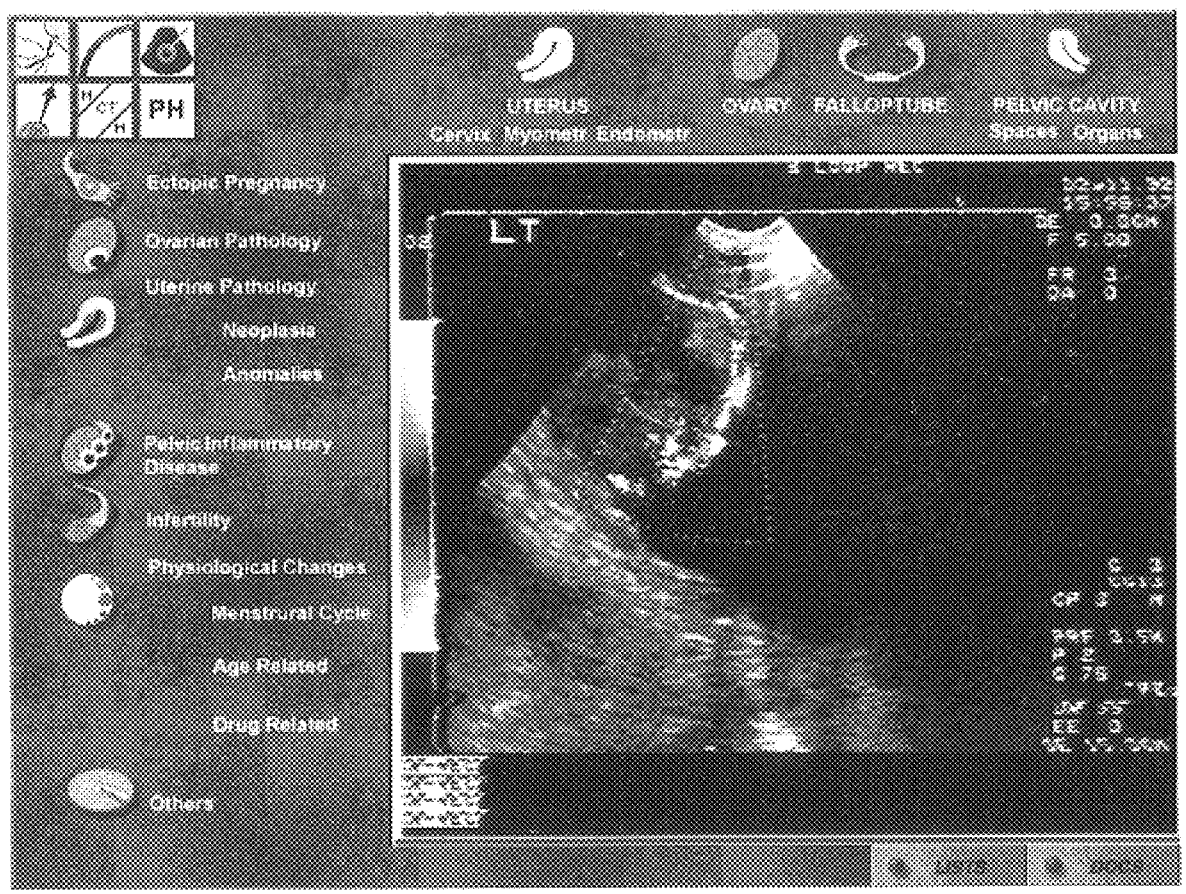
FIG. 5 is a view of a display showing patient data from a sonogram presented in a video display field with organ and condition information surrounding the video display field.

In a preferred embodiment of the invention, during the operation of the adjunct device of the present invention it presents a visual display field from an existing diagnosis device surrounded by an additional video display generated by the invention. An example of a combined video display is shown in FIG. 5.

This additional video display contains a two dimensional matrix of information. Along one dimension are representations of anatomical organs of the site being examined, and which are appropriately examined by the diagnosis device. Along the other dimension are representations of conditions (e.g., symptoms being complained of, where such conditions are capable of examination and diagnosis by the diagnosis device. The matrix display is identified herein as a "Corematrix," for correspondence or correlation matrix.

Figure 14:
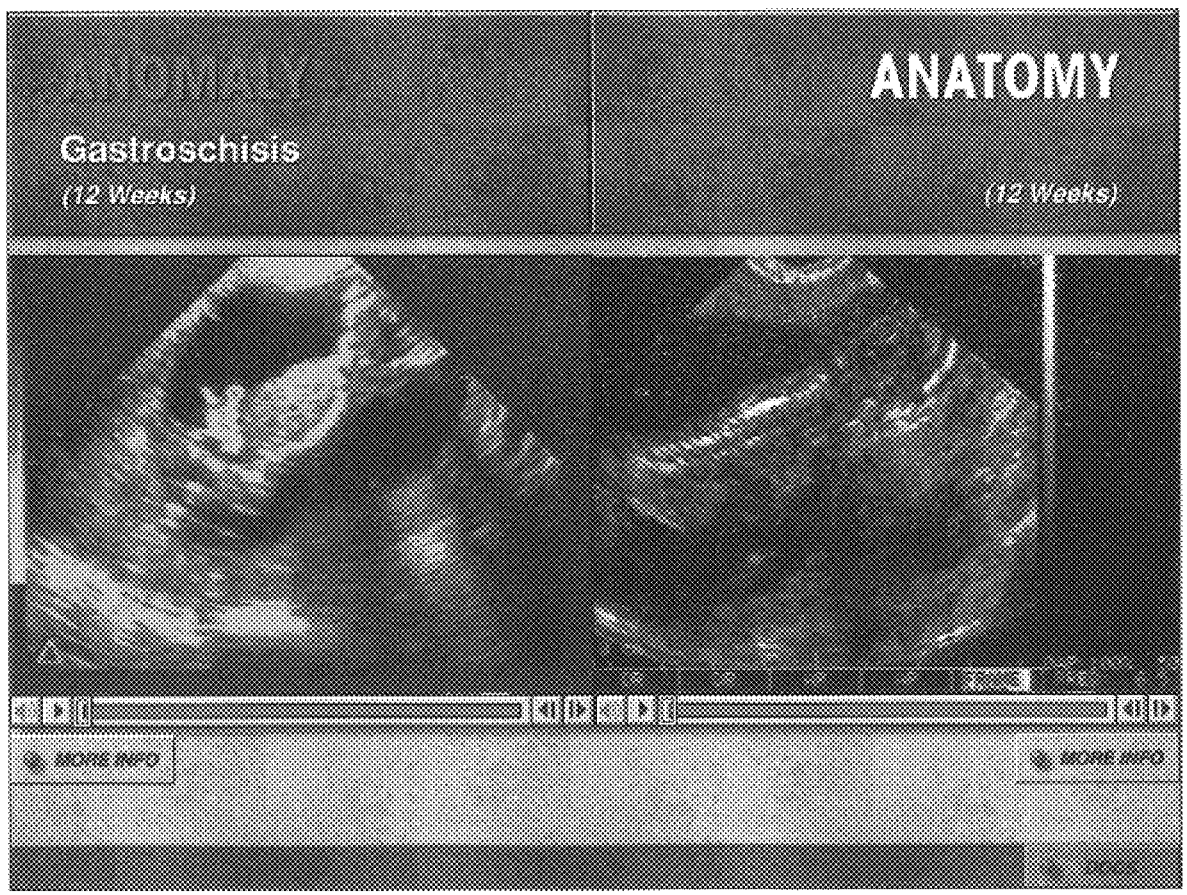
FIG. 14 is a side by side comparison of a fetus with an anomaly as marked as compared to a normal fetus at the same time period.

While the organ and condition representations may be placed in any convenient location on the screen, it is desirable to arrange them so they form a matrix, or Corematrix, from which an intersection is readily apparent. This preferred display conserves most of the display for the purpose of viewing the site of interest by any of the available or future methods of diagnosis. Further, the organs and the conditions may be displayed in text, or they may be represented by icons, or they may be shown by some combination of text and icons, as shown in FIG. 1. The intersection point, when activated, relates the conditions to the organ and the adjunct system evaluates the probability of diagnosis with respect to the condition affecting the organ. The adjunct device also retrieves from a stored library of images corresponding (as imaged by the same diagnostic device) to the organ and having the condition related by the matrix whereby the actual image can be directly compared to an image with the condition as shown in FIG. 14.

Figure 8:
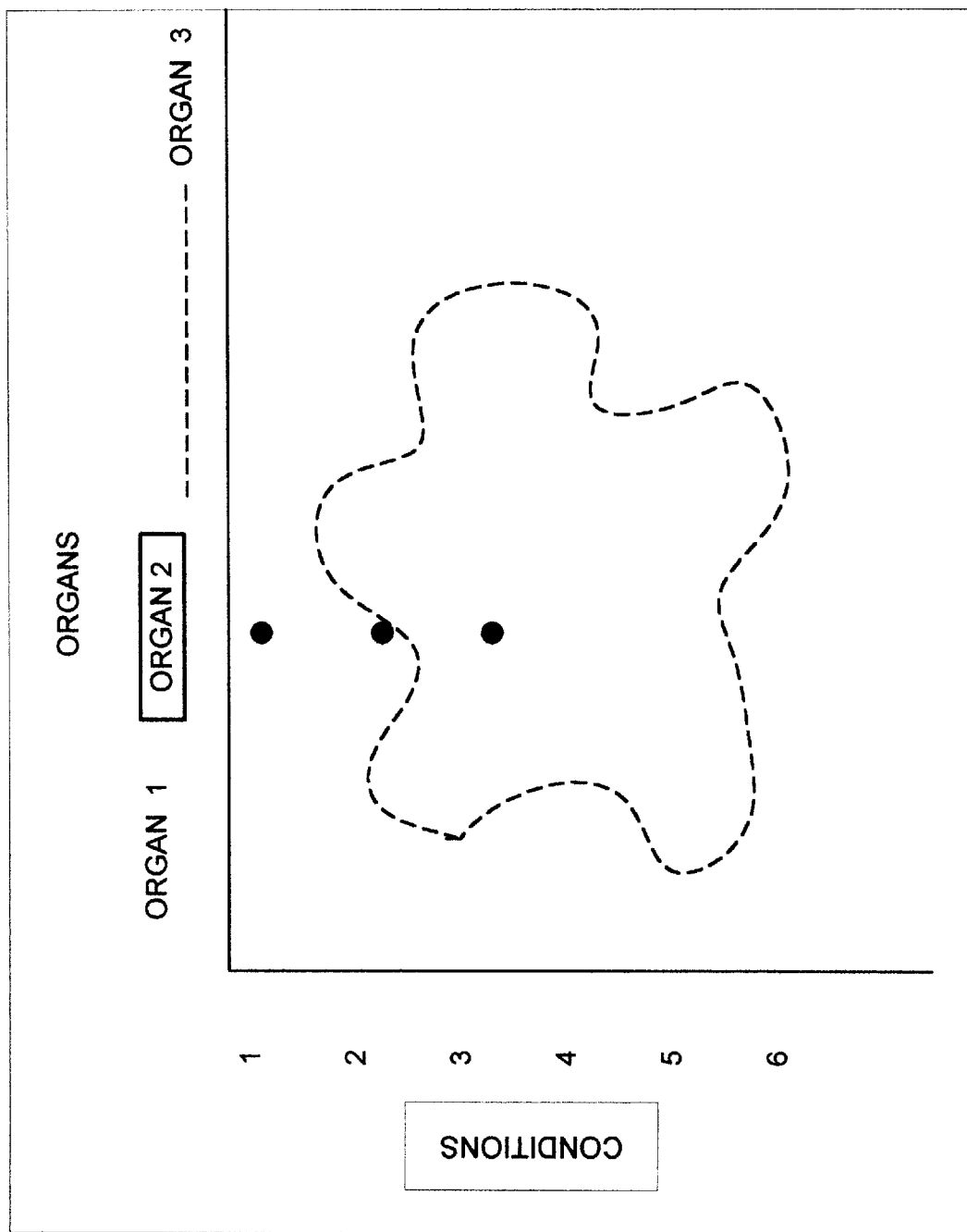
FIG. 8 is a representation of a display showing icons superimposed over patient data.

The adjunct device of the present invention allows for the superimposition of icons over the visual display field, as shown in FIG. 8, where the icons may indicate conditions which affect a represented anatomical organ, or the icons may indicate anatomical organs which may be affected by a represented condition. Alternatively, the visual display field may alternate with a grid display of such icons, as is shown in FIG. 1.

For ease of use and display, this display may not include all possible organs or conditions, but rather identify an organ subsystem or category of conditions. Selection of a displayed organ subsystem or category of conditions will present an alternate two dimensional matrix containing representations of various anatomical organs or organs within a subsystem along one dimensional axis of the matrix, with representations of various conditions or subsets of a category of conditions along the other dimensional axis. The operator or diagnostician may select an icon, superimposed or not, to obtain detailed information about the selected condition as it affects the selected organ. Selection can be accomplished in any way such as with a track ball, mouse or a touch sensitive panel.

Figure 2:
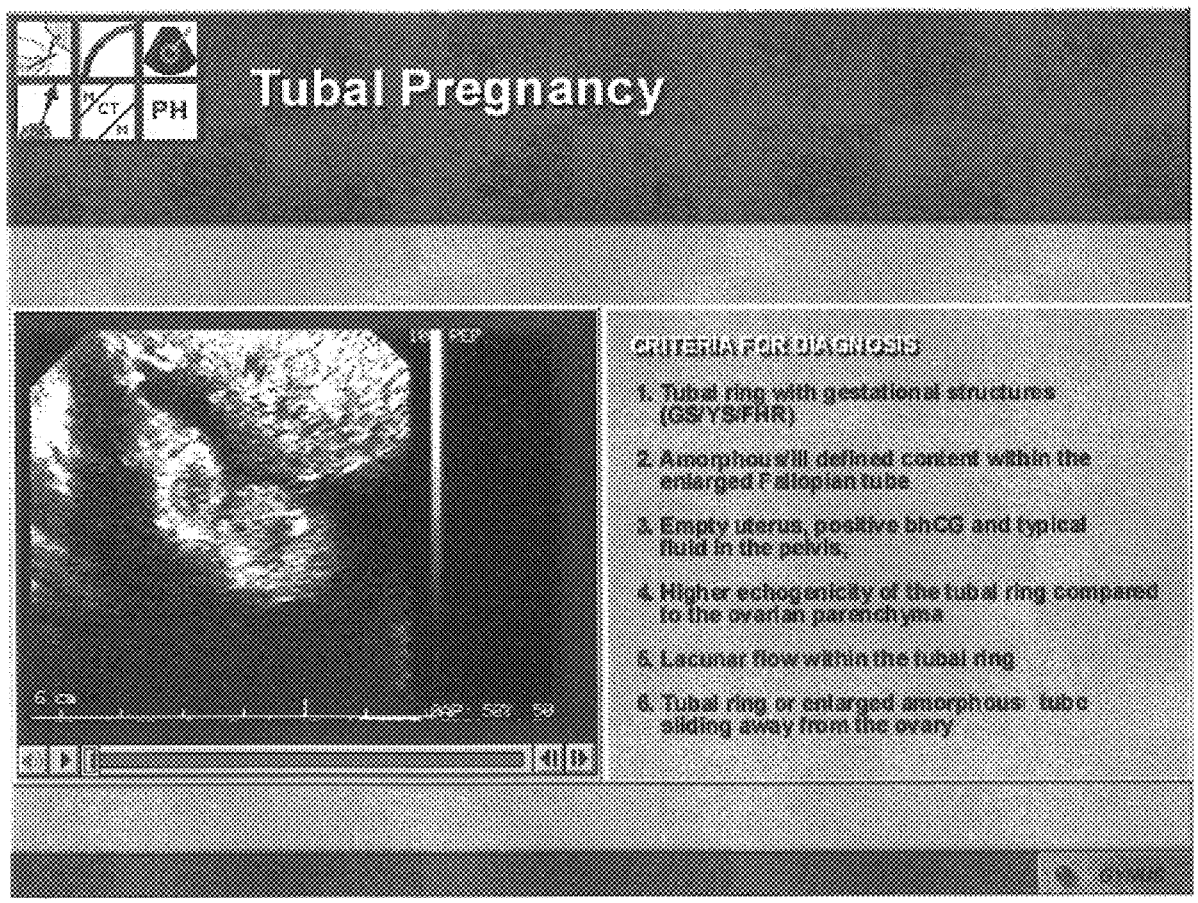
FIG. 2 is a view of a display showing detailed information about a condition, tubal pregnancy, as it affects an organ, the fallopian tubes.
Figure 9:
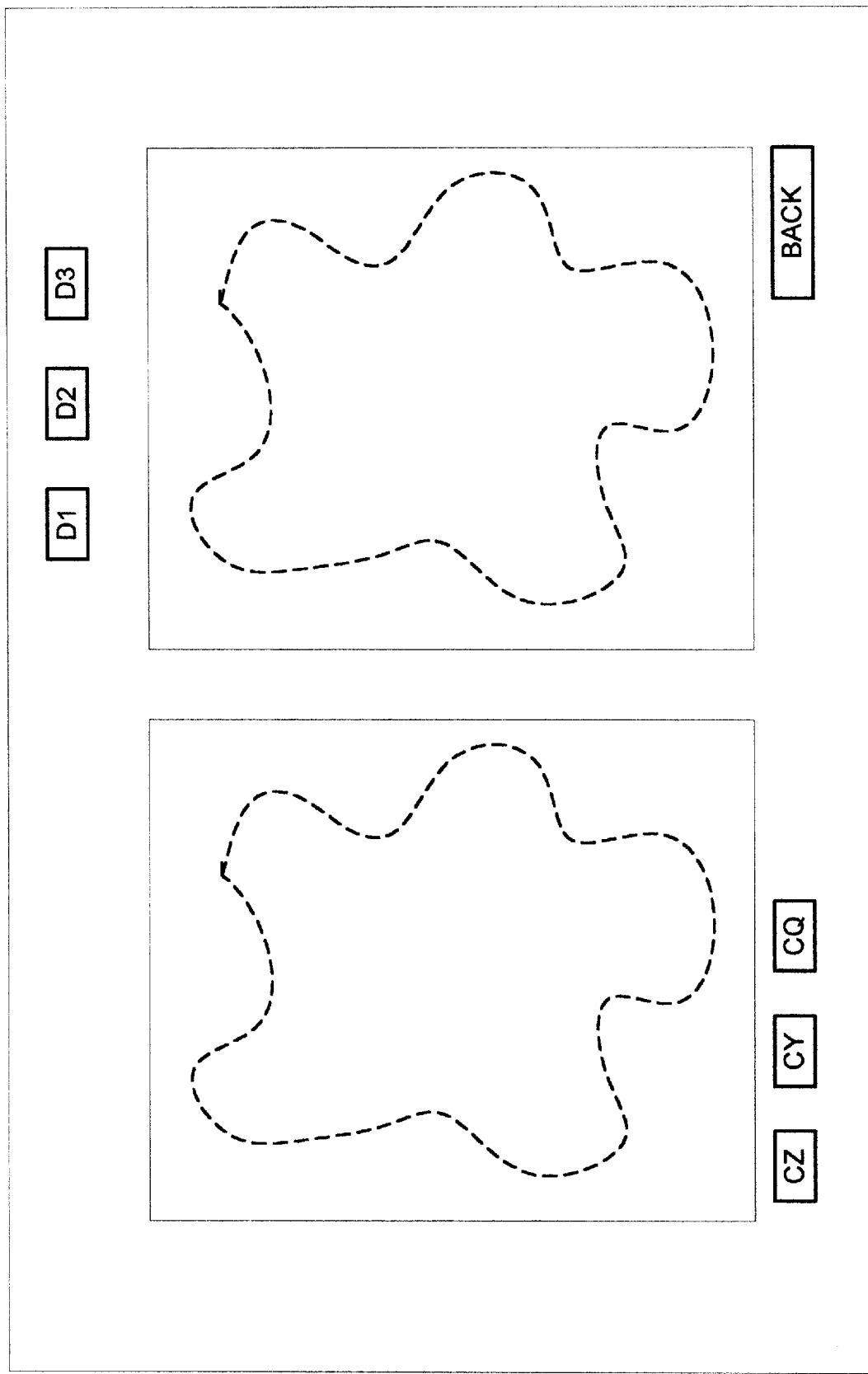
FIG. 9 is a representation of a display showing a side by side comparison of patient data with condition data.

The detailed information preferably includes a visual representation of the condition as it affects the organ in a typical case. The detailed information may also include criteria for the condition, presented in textual or graphic format. FIG. 2 is an example of detailed information of a tubal pregnancy with a video clip of a sonogram of a typical case, along with text identifying criteria for diagnosis of a tubal pregnancy. Patient data may be shown adjacent to typical condition data for ease of analysis, as shown in FIG. 9.

Figure 3:
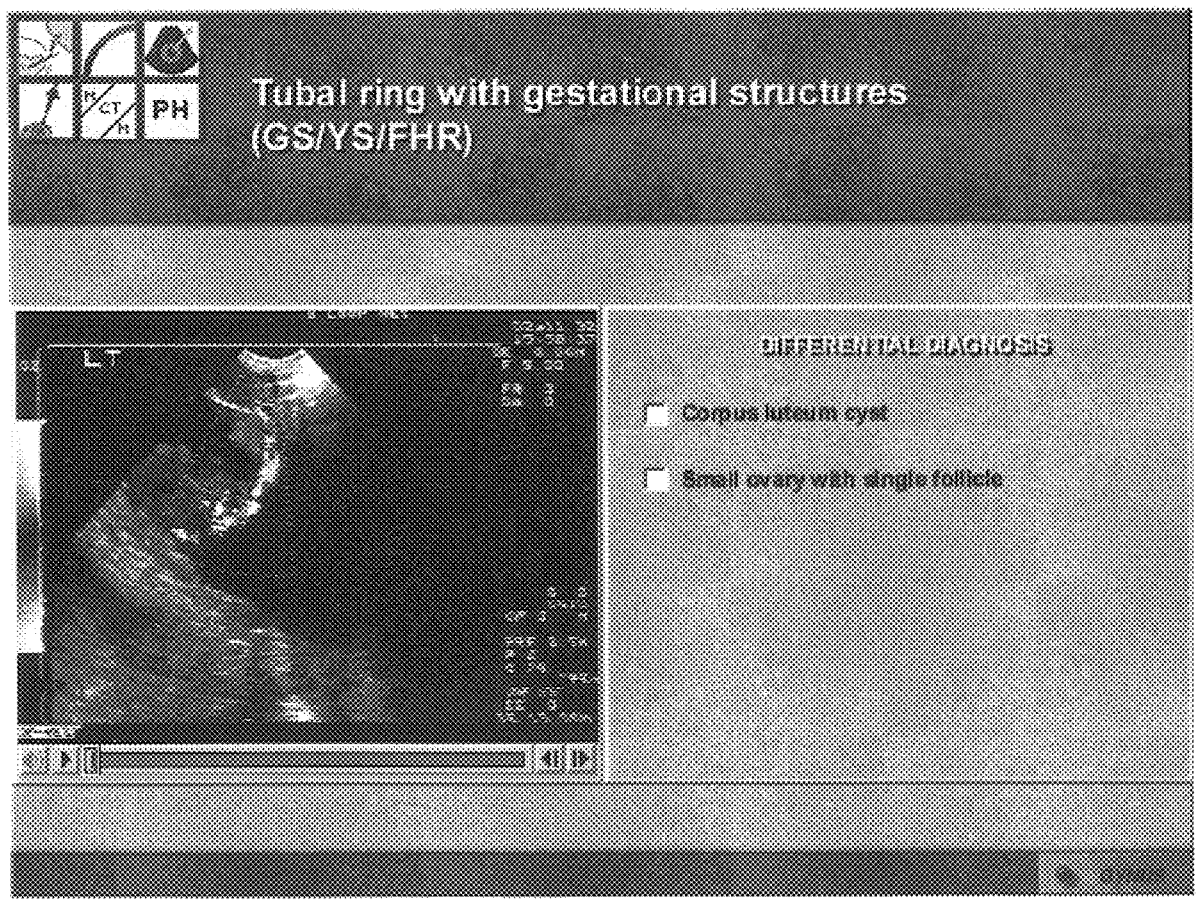
FIG. 3 is a view of a display showing information about one criteria of a tubal pregnancy, identifying differential diagnosis with probabilities of making a mistake in the shown situation.
Figure 4:
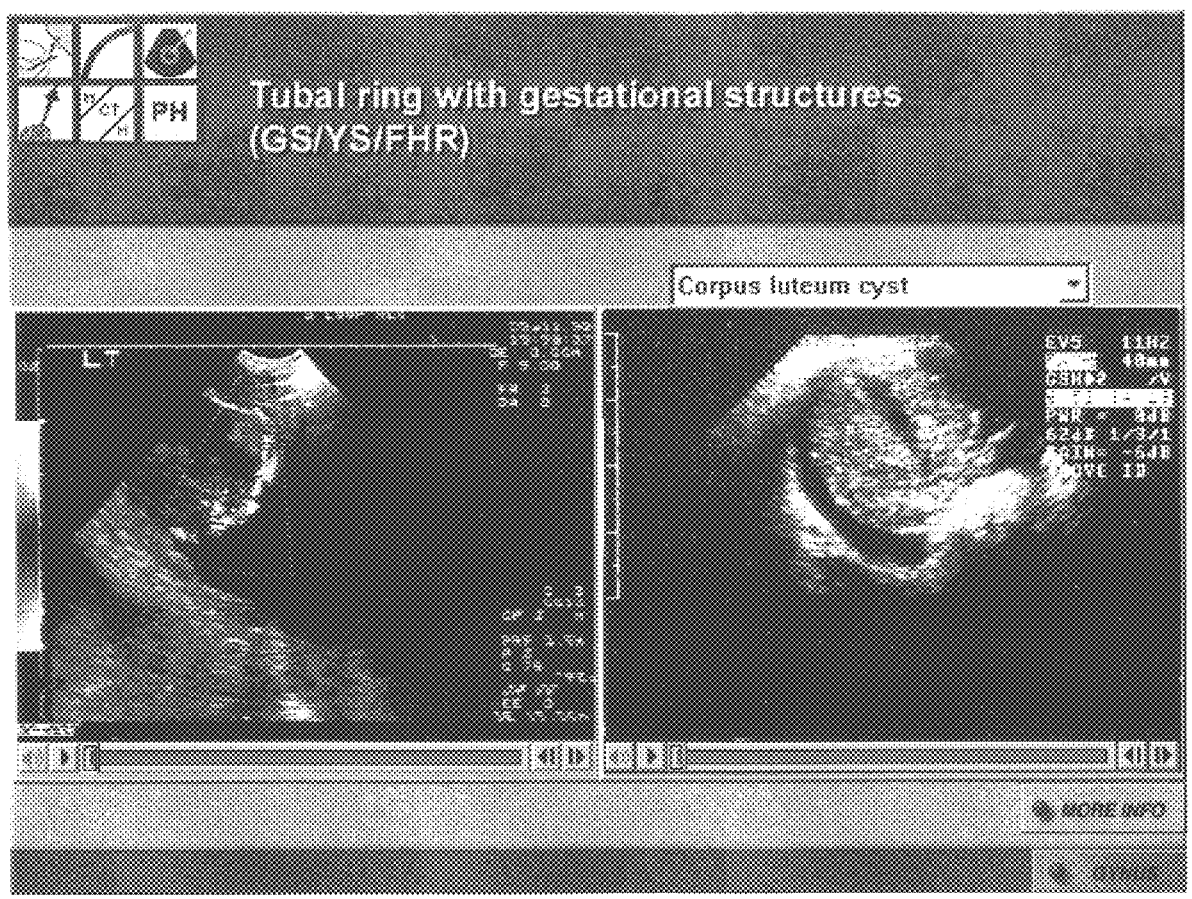
FIG. 4 is a view of a display showing a side by side comparison of a criteria of a tubal pregnancy and a differential diagnosis with potential for mistake in diagnosis.

The operator or diagnostician may select one or more criteria to obtain additional information. Such additional information preferably includes an alternate visual representation of the condition, showing the chosen criteria in greater detail, as shown in FIG. 3. The additional information may also include references to differential diagnoses. Such differential diagnoses are previously categorized and associated with the alternate criteria as selected by the operator.

In a preferred embodiment, the operator would be offered a selection of other conditions that appear similar to the selected condition in the selected organ. These may be listed anywhere on the display, and in any manner, but are preferably listed in thumbnail views on the display below the shown stored image. If any of these conditions are selected, a stored image of the newly selected condition may be displayed in place of the currently shown stored image. And, as above, the operator may be offered a selection of other conditions that appear similar to the selected condition in the selected organ.

Also in a preferred embodiment, the operator is offered a differential diagnosis. For example, the operator may be offered a set of criteria that would also be required to determine that the selected condition is actually present in the selected organ. In FIG. 9, the operator can select any of D1, D2 or D3, and if selected, these would be displayed either in an additional window on the display (not shown) or in place of the stored image For all available or future diagnostic tools it is preferred not to obscure the real-time or post-processing operator's view of the site of interest.

Selection of the presented differential diagnosis by the operator prompts the adjunct device to display a variation of the initial Corematrix screen, highlighting the selected differential diagnosis as a condition, and identifying the various organs which are affected by the selected diagnosis. The operator may select a particular organ affected and repeat the process for the differential diagnosis.

Figure 7:
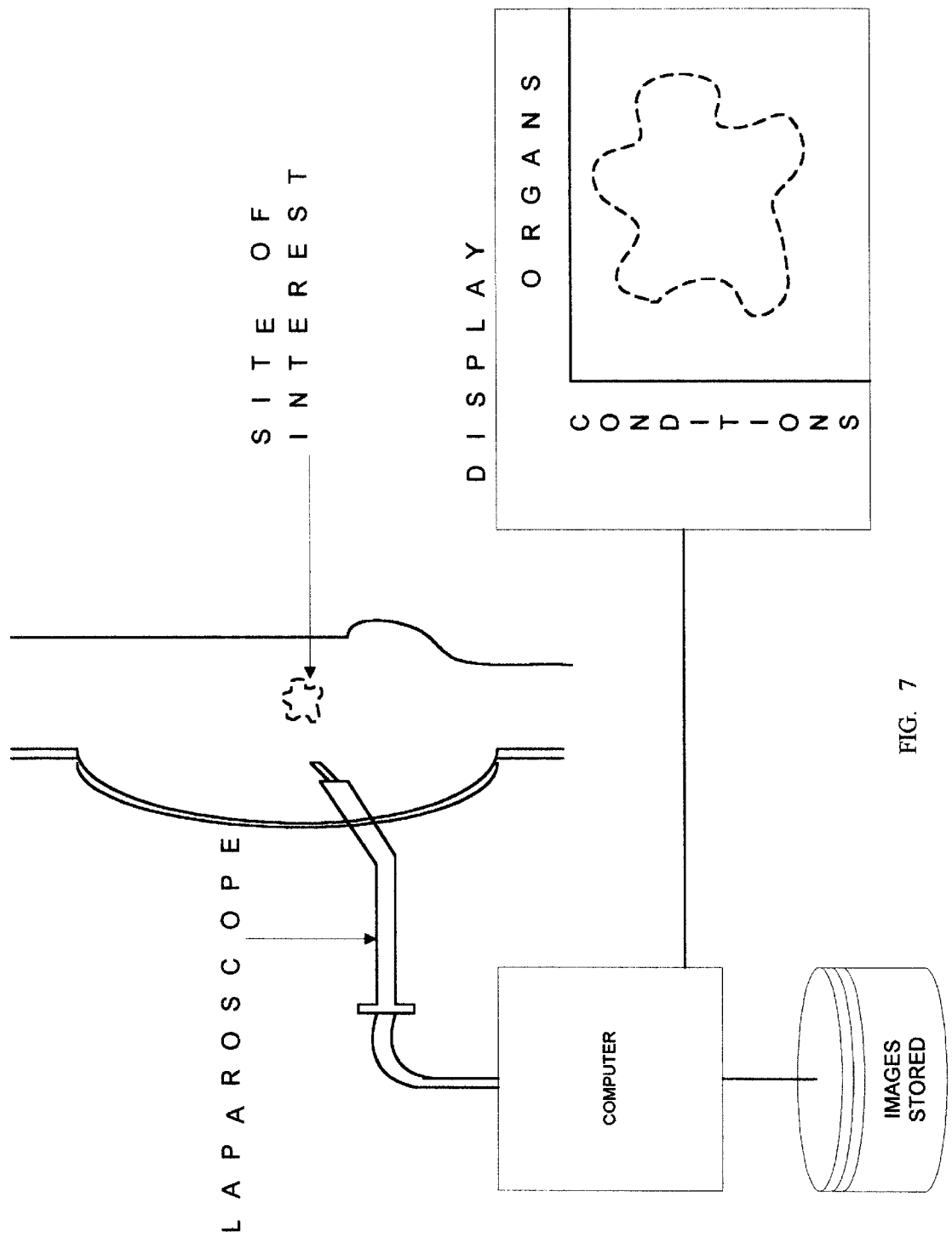
FIG. 7 is a representation of the present invention, operating in conjunction with a laparoscope.

With reference to FIG. 7, and the shown utilization of a laparoscopic for imaging, the laparoscope is provided with a camera that transmits an image of the site of interest to the operator. The image is input into a computer system and output on the television-type display which the operator views to observe the site of interest. The display also comprises representations of organs that may be encountered in the present laparoscopic procedure along the top, and representations of conditions that may be encountered along the left side. When the operator points the laparoscope camera at a particular site of interest, for example, the fallopian tubes, such organ can be selected from the display.

With reference to FIG. 8, once the organ is selected, (organ 2 in FIG. 8) the computer superimposes upon the site display a column of the matrix corresponding to the selected organ, and identifying each of the conditions that would apply to this organ. In a preferred embodiment, this is represented by the presence of some symbol at the matrix cross-point between the organ and the corresponding condition. When the operator detects a condition in the organ, the operator may select from the display the condition believed to be present. If this condition is not one that applies to the organ, the selection may then switch to the most appropriate case (based on preset probabilities). If, however, the condition corresponds to the organ, as shown for example, by the presence of a dot, the operator may select that condition. Selection, as described above, may be done by any known means or method.

With respect to FIG. 9, once both an organ and a condition are selected, the display is changed to simultaneously show the present site of interest in the same field of view with a stored image of the selected organ in the selected condition. The stored image is preferably stored on a storage device, such as CD-ROM or optical disks, or a hard disk drive of the computer (see FIG. 7). The storage device, however, is not important to the invention in that any type of storage device may be used provided that it can store a plurality of images (still or moving), and can selectively retrieve the images. The operator can now simultaneously view the stored image alongside of the actual site of interest.

Figure 10:
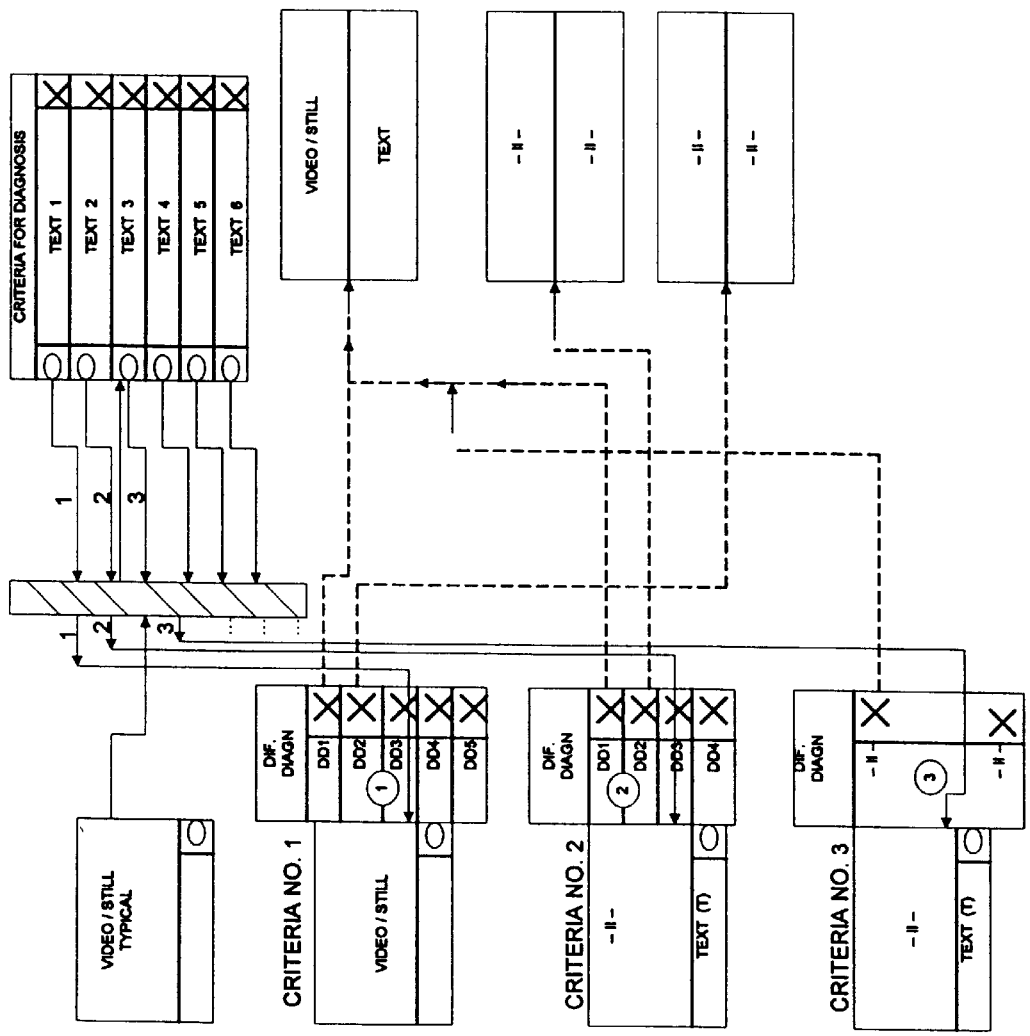
FIG. 10 is a representation of a hierarchical display of the present invention.
Figure 11:
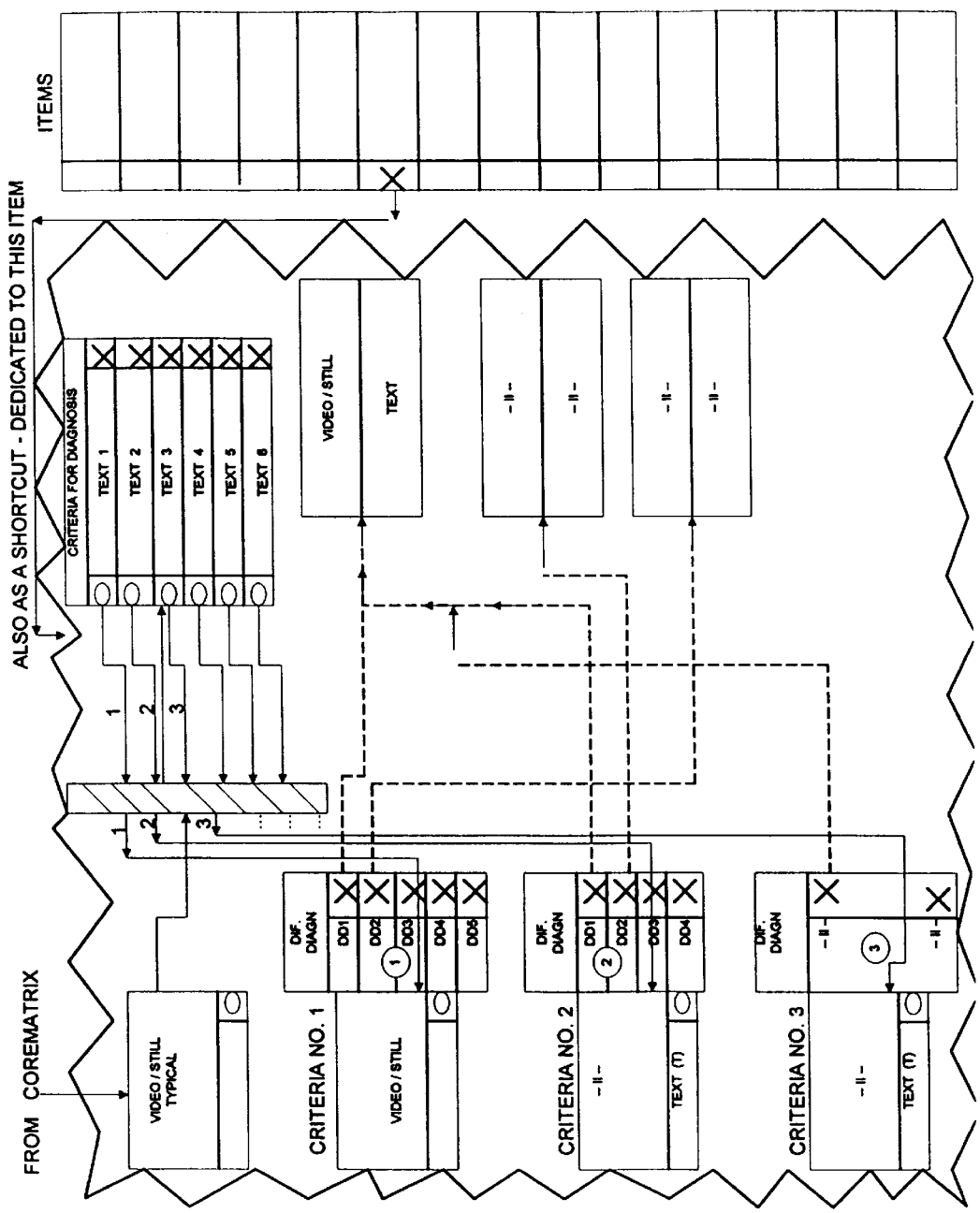
FIG. 11 is a representation showing access routes to the hierarchical display.

The various functions of the invention may be accessed through a master, or hierarchical display, as shown in FIG. 10. The hierarchical display provides an overview of the relations of the various diagnosis points of the invention, whereby the operator may access any given point without having to follow through a prescribed order of steps. FIG. 11 depicts a representation of the relationship between the hierarchical display and access points, such as the Corematrix display of FIG. 1, or through a glossary function as shown in FIG. 12.

The operator may access the medical condition information by way of a glossary function, as shown in FIG. 12. Using the glossary, the database of medical condition information is indexed, according to a set of rules, such as alphabetical by name of the condition. The operator may thereby select a particular medical condition through the glossary. Selection of a medical condition will direct the diagnostic device to the hierarchical page presentation as shown in FIGS. 10 and 11. The operator may navigate through the system as discussed above.

The invention may also be embodied as a stand-alone system, incorporating data from a plurality of diagnostic tools, where the operator may be first presented with a computer screen identifying a plurality of subsystems to choose from. These subsystems may be broken down by various anatomical systems, by disease states, by medical diagnostic device, or by anatomical organ.

Once a subsystem is selected, the operator is presented with a two dimensional Corematrix configuration identifying potential data categories for a given medical diagnostic device, shown in FIG. 1 as ultrasonogram categories of a gynecological subsystem. In a preferred embodiment, the matrix configuration provides representations of various anatomical organs along one dimensional axis of the matrix, with representations of various conditions along the other dimensional axis. A three dimensional matrix may also be utilized, where the third dimension may provide for identification of categories of anatomical organs and conditions related to, or detectable by, different medical diagnosis devices.

The operator's selection of one of the organ representations will result in the invention identifying conditions affecting the represented organ and provide a series of "hot-spots" for the operator to select. The invention may thereby be utilized as discussed above.

Although the above description is described with reference to a laparoscope, it would be similar for any other tool disclosed above. Where the tool does not have its own display, numerous options are available. First, it is possible to implement the above-described invention within the field of view of, for example, a microscope or otoscope where the outer perimeter of a generally circular view could be used to present organs and conditions (rather than the top and side of a rectangular screen). Alternatively, it is possible to implement the above-described invention within the field of view of a purely mechanical device, as a speculum, by fastening a display screen to the device which provides for a simultaneous viewing of the site of interest and display of stored images.

In lieu of the side by side analysis it is also within the ambit of the invention to accept an output from an existing diagnostic tool and superimpose the stored image and the selection images upon it, or to feed the stored image and the selection images to the existing tool and have the existing display provide all of the necessary information in the operator's field of view.

The stored library images that are displayed for comparative purposes may be from a variety of data, such as previous images of the same organ in the present patient at an earlier date. In another preferred embodiment one or more stored image for each organ-condition combination are used to represent the typical or expected image of the condition in that organ.

It is also preferred that the computer be able to color balance or image process the stored image to match the environment of the laparoscope, or to permit setting of color balance controls or other imaging controls (which may include, e.g., zoom, scale, etc.) by the operator.

It is understood that stored images include both still and moving images, to include examination of a site of interest in an organ that normally moves perceptibly, as would be the case with the heart.

Figure 6:
FIG. 6 is a view of a display showing fetal information arranged by organ system and time-oriented development stage.
Figure 13:
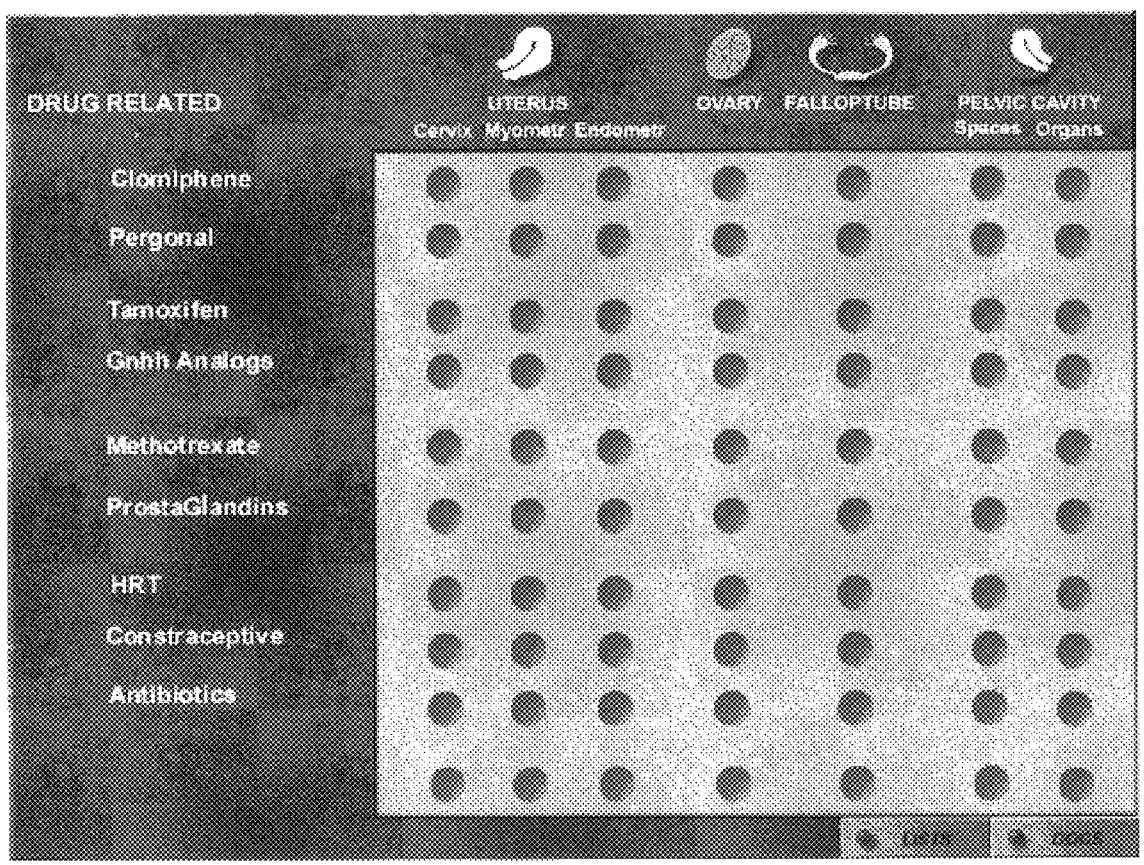
FIG. 13 is a view of a display showing a correlation matrix identifying organs and a list of drugs for diagnosis with respect to interactions.

Though this description has been given with an organ bias, it is also possible to first select a condition, and then select the organ affected. In other words, it is possible to carry out the invention with a condition bias. Alternatively, information about drugs or time periods may be utilized, as shown in FIGS. 6 and 13.

Figure 15:
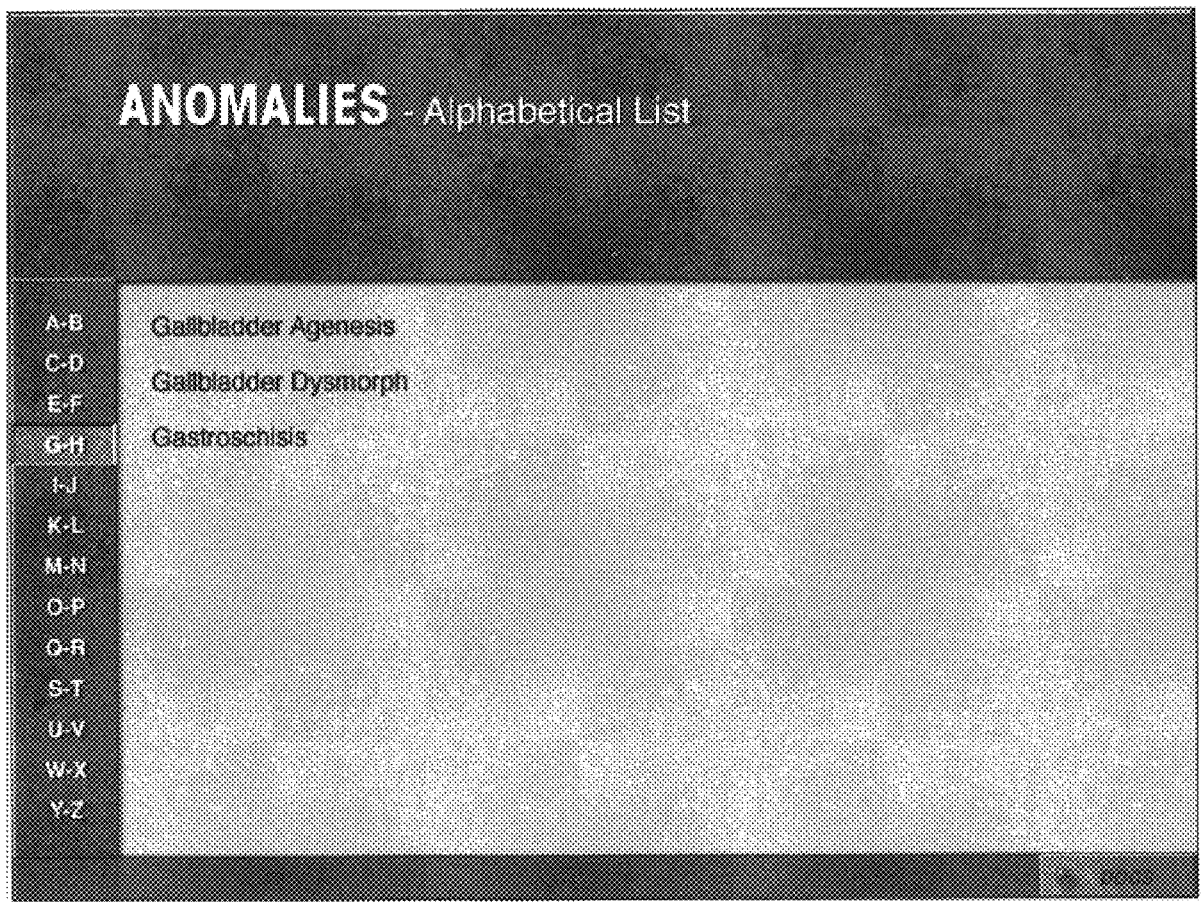
FIG. 15 is an example of a listing of fetal anomalies which leads to the matrix shown in FIG. 1.
Figure 16:
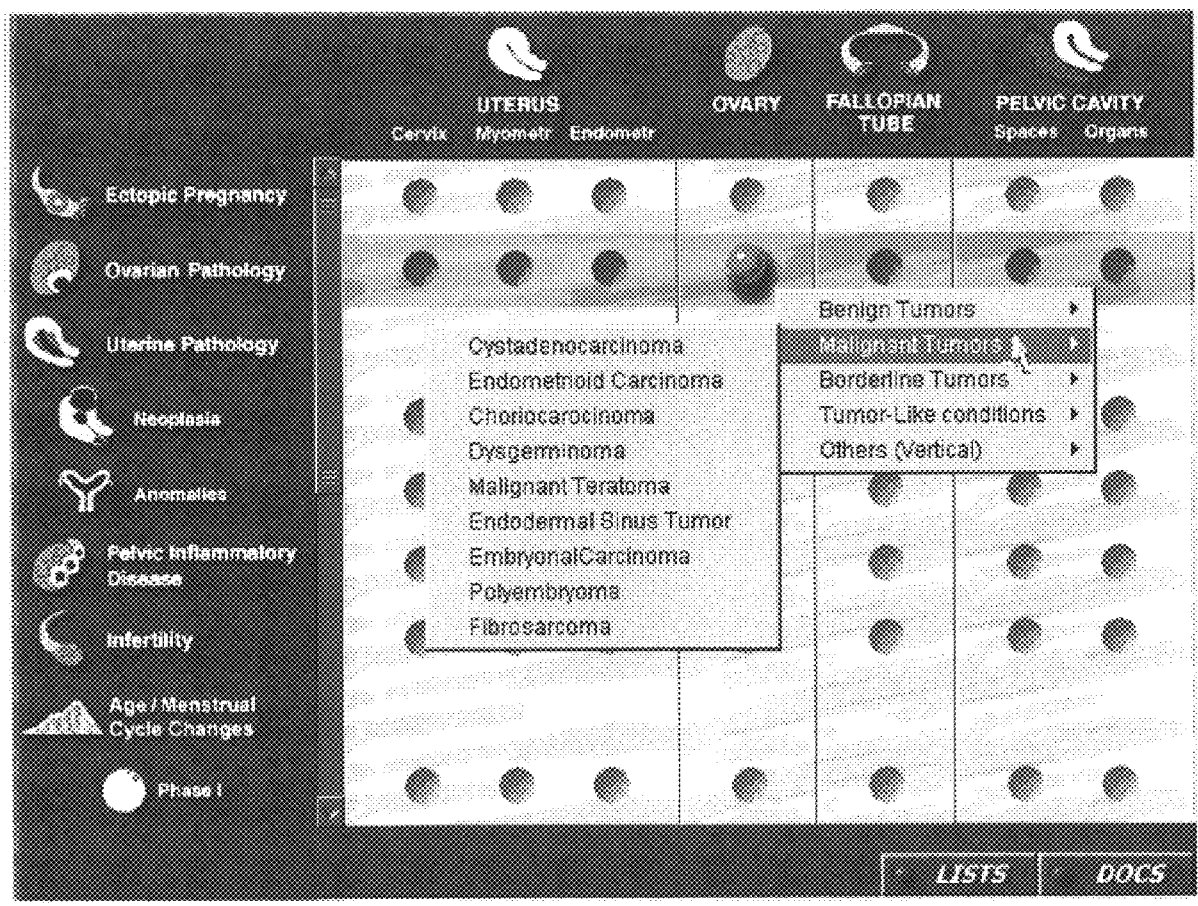
FIG. 16 is the matrix showing classification of iseases according to benign, malignant, borderline, tumorlike and other conditions and list of malignant tumors.

With respect to FIGS. 15 and 16, clicking on the appropriate button provides return and activation of the matrix.

It is possible, without departing from the spirit of the invention to supply substantial additional information to the operator's field of view. For example, in some applications, it would be preferred to include additional diagnostic information, drug interactions, etc.

It is understood that the above description and drawings are merely exemplary of the present invention and that changes in matrixes, organs being scanned or screened and conditions may be made without departing from the scope of the present invention. In addition, changes may be made to the manner and type of information and images being provided as well as the subject matter being examined. Thus, there is, in addition to application to medical diagnoses, similar application to any field requiring a diagnosis such as instrument examination of machines, and objects such as airplanes and the like, subject to varying conditions (e.g., metal fatigue, rust, leaks, etc.) and requiring diagnosis and comparison to existing established criteria for defects and conditions. These and other changes and modifications are possible without departing from the scope of the present invention as defined in the following claims.

What is claimed is:

1. An adjunct device and system for use with an existing diagnostic object or body imaging device, said adjunct device comprising:

a) means for providing comparative images to directly compare on a single display an image of an object or body obtained from the imaging device and one or more library stored images from the same type of imaging device of a corresponding object or body having probable conditions as the object or body being imaged, the probable conditions being determined either by the user or by a computerized comparison of the image to the library stored images falling within preset comparison parameters; whereby a probable diagnosis of an actual condition of the object or body can be formulated by a matching comparison;

b) means for providing a weighted probability for a particular diagnosis being relevant to said condition, said weighted probability being based on library stored general parameters and optionally in further view of the prior history of the body or object;

c) means for providing a weighted probability for a particular mistake being relevant to the condition and image based on library stored general parameters and optionally in further view of the prior history of the body or object and present image on the screen;

d) means for providing to the user, if relevant, which additional test or tests are required to increase the probability of relevance of a probable diagnosis;

e) means for providing to the user a case and situation oriented need for follow-up and/or monitoring of conditions; and f) means for providing to the user, information regarding treatment or repair protocols, as relevant to the body or object, for a diagnosis with a probability above a pre-set probability level.

2. The adjunct device of claim 1 wherein the condition is a medical condition and the imaging device is adapted for imaging of human body parts or organs.

3. The adjunct device of claim 1 wherein the condition is a mechanical condition of a machine or device.

4. The adjunct device of claim 1 wherein the means for providing weighted probability for a particular mistake being relevant also provides a showing of probable errors with respect to a particular image selected from the library stored images.

* * * * *